United States Patent [19]

Brain

[11] Patent Number: 4,509,514
[45] Date of Patent: Apr. 9, 1985

[54] ARTIFICIAL AIRWAY DEVICE

[76] Inventor: Archibald I. J. Brain, Flat 1, 6 Claremont Rd., Folkestone, Kent, England

[21] Appl. No.: 449,728

[22] Filed: Dec. 14, 1982

[30] Foreign Application Priority Data

Dec. 16, 1981 [GB] United Kingdom ............... 8137899

[51] Int. Cl.³ .......................................... A61M 25/00
[52] U.S. Cl. .................................. 128/207.15; 604/96
[58] Field of Search ................ 128/207.15, 206.26; 604/96–103

[56] References Cited

U.S. PATENT DOCUMENTS 2,099,127 11/1937 Leech .......................... 128/207.15
2,175,726 10/1939 Gebauer ....................... 128/207.15
3,417,744 12/1968 Miskin et al. ................. 604/101 X
4,351,342 9/1982 Wiita et al. ........................ 604/43

Primary Examiner—Dalton L. Truluck
Attorney, Agent, or Firm—Sughrue, Mion, Zinn, Macpeak and Seas

[57] ABSTRACT

An artificial airway device, for use in place of an endotracheal tube to facilitate lung ventilation in an unconscious patient, is in the form of a laryngeal mask comprising a tube opening into the interior of a mask portion whose periphery, which may be inflatable, is adapted to seal around the inlet to the larynx, thus securing the patient's airway, permitting spontaneous or controlled ventilation and preventing inhalation of extraneous matter.

5 Claims, 3 Drawing Figures

4,509,514

ARTIFICIAL AIRWAY DEVICE

BACKGROUND OF THE INVENTION

1. Field of the Invention

This invention relates to an artificial airway device to facilitate lung ventilation in an unconscious patient, and more specifically to such a device designed for placing in the oropharynx of the patient in order to prevent airway obstruction, to permit either spontaneous or controlled ventilation and to prevent the inhalation into the lungs of extraneous matter such as blood or vomit.

2. Description of the Prior Art

To maintain the airway of an unconscious patient, and to achieve the three objectives mentioned above, it is normal practice in general anaesthesia to use an endotracheal tube, which is a flexible tube of rubber or plastics, usually with an inflatable cuff around the distal end. Alternatively, an oro- or naso-pharyngeal airway may be used, which is a flexible tube extending from the mouth or nose into the pharynx but not into the larynx. In anaesthesia, such an airway is used in conjunction with a face mask, unlike the endotracheal tube. While preventing obstruction of the airway by the tongue, the oro- or naso-pharyngeal airway cannot be used for controlled ventilation and does not prevent inhalation of extraneous matter.

The endotracheal tube is introduced through the larynx into the trachea or windpipe, whereupon the cuff is inflated through a small auxiliary tube to seal against the wall of the trachea. Introduction of the endotracheal tube is a skilled operation normally requiring use of a laryngoscope to guide the tube through the larynx, past the vocal cords and into the trachea. There is a risk that the tube or the laryngoscope may cause damage to soft tissues or to the sensitive structures of the larynx. It is not always possible to see the larynx, making intubation difficult or impossible in some patients. There can be a risk of accidental intubation of the oesophagus or of the right or left main bronchus. Placing of the tube in the trachea effectively narrows the interior passage of lumen of the trachea and provides a potential source of damage through infection or pressure while preventing normal upward flow of mucus from the trachea and rendering effective coughing impossible.

SUMMARY OF THE INVENTION

It is an object of the present invention to provide an artificial airway device which will retain the advantages of the endotracheal tube but will avoid the foregoing disadvantages and which will also be more versatile than the known oro- or naso-pharyngeal airways.

According to the invention, an artificial airway device comprises a curved or flexible tube opening at one end into the interior of a hollow mask portion shaped to conform to and to fit readily into the actual and potential space behind the larynx and to seal around the circumference of the laryngeal inlet without penetrating into the interior of the larynx. The device thus constitutes a laryngeal mask. The mask portion of the device may have an inflatable periphery which is adapted to form the seal around the laryngeal inlet. Alternatively or in addition, the mask portion may have an inflatable posterior part which is adapted to press against the back of the throat and thereby increase the sealing pressure around the laryngeal inlet.

The shape and (when fitted) the inflatable part or parts of the mask ensure that it approximates closely to the shape of the space between the laryngeal inlet and the walls of the lower part of the throat behind it. Since the walls of tissue forming the back of the throat are relatively rigid, inflation of the mask forces it more tightly against the tissues surrounding the laryngeal inlet, so forming an airtight seal, while tending to anchor the mask in position.

Insertion of the device has been found to be easy and convenient in the majority of patients, especially if initially it is inserted through the mouth with the interior of lumen of the mask facing backwards to facilitate negotiation of the angle behind the tongue. The mask is then gently rotated through 180° to face forwards as it is pushed down into position. When the distal tip of the mask reaches the upper end of the oesophagus, a definite end-point can be felt, indicating that the mask is correctly placed. The mask may then be inflated to form the airtight seal. A laryngoscope is not usually required. The mask does not enter the larynx or trachea so the risk of damage to these structures is avoided and the tracheal lumen is not narrowed as it is by insertion of an endotracheal tube. The risk of accidental entry into the oesophagus or one of the main bronchi is also avoided. Once in place the laryngeal mask generally permits the lungs to be ventilated by positive pressure. Alternatively the patient may be permitted to breathe spontaneously.

The mask portion of the device may be formed of flexible rubber or plastics material with a tubular element of the same material forming its inflatable periphery and/or posterior part. The mask portion may be made separately from the curved or flexible tube and secured thereto in an airtight manner. Preferably, in that case, the end of the flexible tube which opens into the interior of the mask portion is cut off at an angle to the length of the tube to provide a semi-rigid spine for the mask.

DETAILED DESCRIPTION OF THE INVENTION

Figure 1:
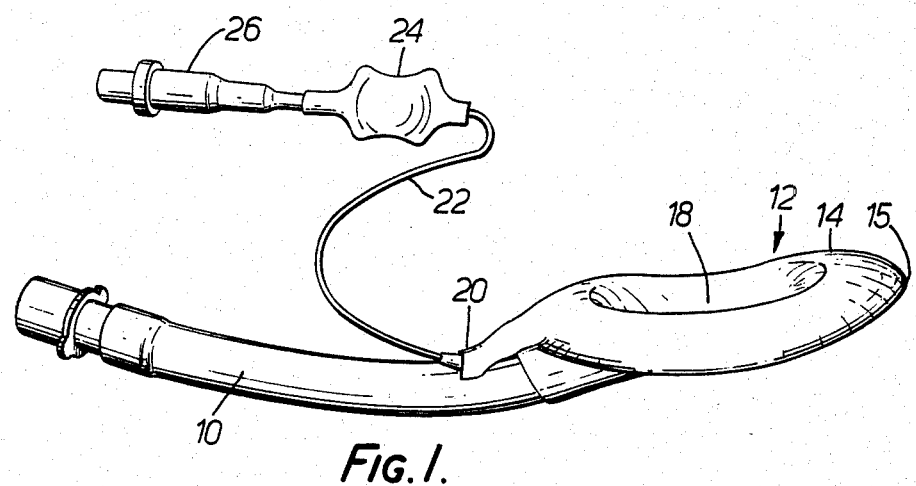
FIG. 1 is a perspective view of an artificial airway device in the form of a laryngeal mask.
Figure 2:
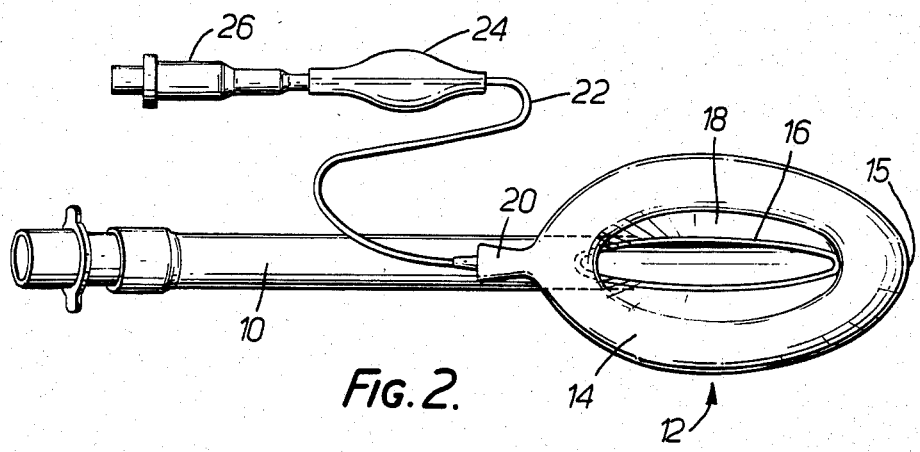
FIG. 2 is a plan view of the device with the periphery of the mask portion inflated.

The laryngeal mask illustrated in the drawings comprises a flexible tube 10 of soft plastics material, similar to that conventionally used for endotracheal tubes made by Portex Limited of Hythe, Kent, England, and a mask portion 12 of flexible rubber sheet material with an inflatable tubular ring 14 of the same rubber material forming its periphery. The distal end 16 of the plastics tube 10 opens into the interior or lumen 18 of the mask portion 12, being cut off at an angle to the length of the tube to provide an elongated elliptical opening, and being sealed into the mask 12 in an airtight manner so as to form a semi-rigid spine for the mask. The inflatable rubber ring 14 is of roughly elliptical shape as seen in plan (FIG. 2) though its distal end 15 may be slightly pointed to conform with the triangular shape of the base of the hypopharynx where it becomes continuous with the upper end of the oesophagus. The ring 14 is formed with a port 20 into which is sealed one end of a flexible plastics tube 22 of much smaller diameter. The other end of tube 22 is provided with an inflation indicator 24 of known type and a non-return valve 26, and can be connected to a small pump (not shown) such as a disposable 20 ml. medical syringe for inflation of the ring 14.

Figure 3:
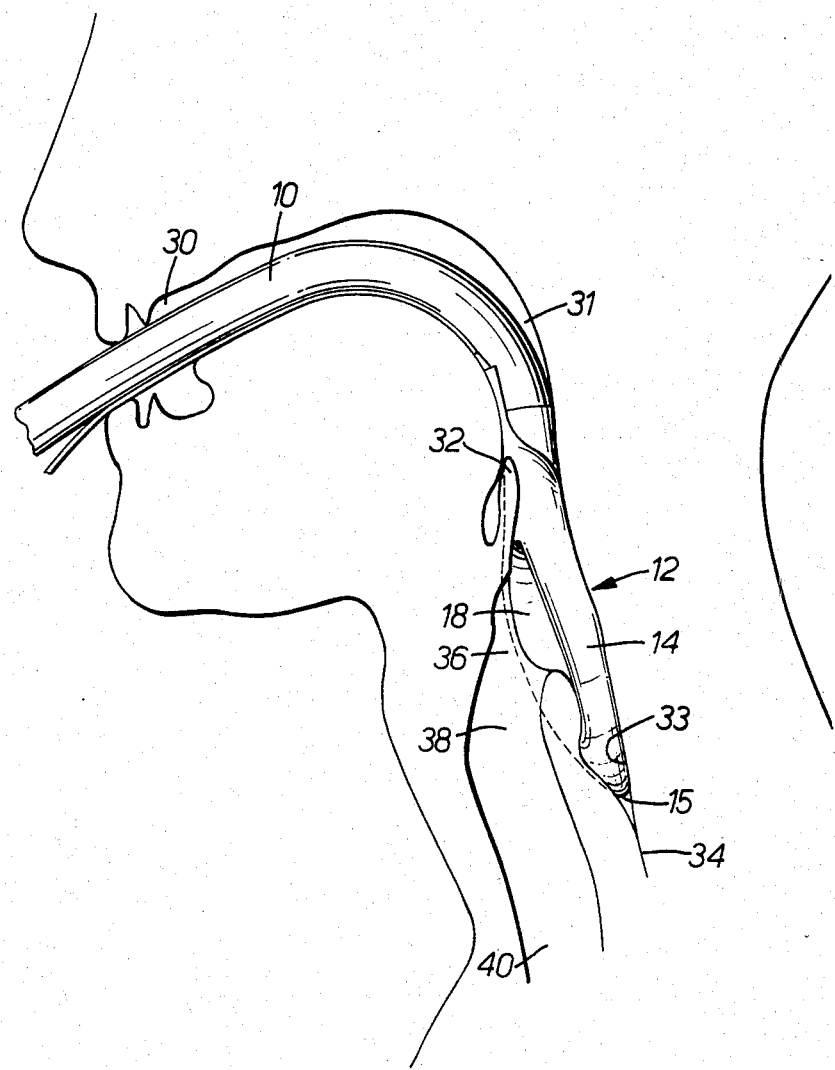
FIG. 3 shows diagrammatically the device in position for use in a patient.

In use, the device is inserted as described above and as shown in FIG. 3 through the patient's mouth 30 and down through the throat 31 past the epiglottis 32 until the mask 12 comes to rest with the distal end 15 of the ring 14 in the base 33 of the throat, lying against the upper end of the normally closed oesophagus 34 which the mask cannot easily enter because of its size and shape. The ring 14 is then inflated as shown to seal around the inlet 36 to the larynx 38. The patient's airway is thus secure and unobstructed and the laryngeal mask can be connected directly to conventional anaesthetic circuit hosing for either positive pressure or spontaneous breathing.

While the embodiment of the invention described above employs an inflatable peripheral ring 14, the mask portion 12 may also, or alternatively, have an inflatable posterior part which, by pressing against the back of the throat on inflation, will increase the sealing pressure around the laryngeal inlet.

The embodiments so far described are adapted for use as disposable instruments, but the laryngeal mask can also be made re-usable.

Where the laryngeal mask is intended to be a reusable instrument, the tube and mask portion may be made of a relatively rigid sterilisable material, e.g. of metal, shaped as described above to conform to and fit readily into the actual and potential space behind the larynx and to seal around the laryngeal inlet. The reference to actual and potential space will be understood to refer to the space normally available and that which can become available on flexure of the surrounding structures.

I claim:

1. An artificial airway device to facilitate lung ventilation in an unconscious patient, comprising a curved or flexible tube and a mask portion carried at one end of the tube, the mask portion having a soft flexible annular peripheral formation which surrounds a hollow interior space or lumen of the mask, said annular peripheral formation of the mask being pre-formed with a roughly elliptical shape capable of conforming to, and fitting readily within the actual and potential space behind the larynx and to form a seal around the circumference of the laryngeal inlet without the device penetrating into the interior of the larynx, the tube opening into the lumen of the mask to provide the airway with the axis of the tube substantially aligned with the length of the roughly elliptical annular periphery of the mask.

2. An artificial airway device according to claim 1, wherein the annular peripheral formation of the mask portion is inflatable to form or improve the seal around the laryngeal inlet.

3. An artificial airway device according to claim 1 wherein the mask portion is made separately from the curved or flexible tube and is secured thereto in an airtight manner.

4. An artificial airway device according to claim 3 wherein the end of the tube which opens into the interior of the mask portion is cut off at an angle to the length of the tube.

5. An artificial airway device according to claim 2 wherein the mask portion is formed of flexible rubber or plastics material with a tubular element of the same material forming its inflatable peripheral formation.

* * * * *